United States Patent
Taylor et al.

(10) Patent No.: US 11,237,168 B2
(45) Date of Patent: Feb. 1, 2022

(54) METHOD FOR IDENTIFYING MODULATORS OF G3BP ACTIVITY

(71) Applicant: St. Jude Children's Research Hospital, Memphis, TN (US)

(72) Inventors: J. Paul Taylor, Memphis, TN (US); Peiguo Yang, Memphis, TN (US); Wenwei Lin, Memphis, TN (US); Taosheng Chen, Memphis, TN (US)

(73) Assignee: ST. JUDE CHILDREN'S RESEARCH HOSPITAL, Memphis, TN (US)

( * ) Notice: Subject to any disclaimer, the term of this patent is extended or adjusted under 35 U.S.C. 154(b) by 302 days.

(21) Appl. No.: 16/453,313

(22) Filed: Jun. 26, 2019

(65) Prior Publication Data

US 2020/0408759 A1 Dec. 31, 2020

(51) Int. Cl.
*G01N 21/64* (2006.01)
*G01N 33/573* (2006.01)

(52) U.S. Cl.
CPC ....... *G01N 33/573* (2013.01); *G01N 21/6428* (2013.01); *G01N 2021/6441* (2013.01); *G01N 2333/914* (2013.01); *G01N 2500/02* (2013.01)

(58) Field of Classification Search
CPC ............. G01N 33/573; G01N 21/6428; G01N 2021/6441; G01N 2500/02; G01N 2333/914
See application file for complete search history.

(56) References Cited

PUBLICATIONS

Brangwynne et al. (U.S. Appl. No. 62/719,751, filed Aug. 20, 2018) (Year: 2018).*
Kedersha et al. (2016) G3BP-Caprin1-USP10 complexes mediate stress granule condensation and associate with 40S subunits. J. Cell Biol. 212(7):845-680.
Panas et al. (2015) Viral and Cellular Proteins Containing FGDF Motifs Bind G3BP to Block Stress Granule Formation. PLoS Pathog. 11(2):e1004659.
Reineke et al. (2015) Stress Granules Regulate Double-Stranded RNA-Dependent Protein Kinase Activation through a Complex Containing G3BP1 and Caprin1. mBio 6(2):e02486.
Solomon et al. (2007) Distinct Structural Features of Caprin-1 Mediate Its Interaction with G3BP-1 and Its Induction of Phosphorylation of Eukaryotic Translation Initiation Factor 2alpha, Entry to Cytoplasmic Stress Granules, and Selective Interaction with a Subset of mRNAs. Mol. Cell. Biol. 27(6):2324-2342.
Soncini et al. (2001) Ras-GAP SH3 domain binding protein (G3BP) is a modulator of USP10, a novel human ubiquitin specific protease. Oncogene 20(29):3869-79.
Tourriere et al. (2003) The RasGAP-associated endoribonuclease G3BP assembles stress granules. J. Cell Biol. 160(6):823-831.

* cited by examiner

*Primary Examiner* — Jeremy C Flinders
(74) *Attorney, Agent, or Firm* — Licata & Tyrrell P.C.

(57) ABSTRACT

A method of identifying a lead or candidate compound that modulates the activity of GTPase-Activating Protein SH3 Domain-Binding Proteins (G3BP) is provided, which includes determining whether a compound modulates the interaction between the N-terminal Nuclear Transport Factor 2-like (NTF2L) domain of G3BP and FGDF peptide of ubiquitin specific protease 10 (USP10) or non-structural protein 3 (nsP3).

5 Claims, No Drawings

Specification includes a Sequence Listing.

METHOD FOR IDENTIFYING MODULATORS OF G3BP ACTIVITY

BACKGROUND

Stress granules are non-membranous assemblies of mRNA and protein (mRNP) that form when translation initiation is limiting, which occurs during many stress responses including glucose starvation, heat stress, osmotic stress, and oxidative stress. Stress granules are thought to influence mRNA function, localization, and to affect signaling pathways. Normally, stress granule formation is a dynamic, reversible process that relies on particular RNA-binding proteins that harbor self-interacting domains of low sequence complexity (LC domains). However, a disturbance in the assembly and/or dynamics of these structures is closely associated with a wide array of human diseases, including cancer, infectious diseases and neurodegenerative diseases such as Alzheimer's, Huntington's, Parkinson's, frontotemporal dementia (FTD), and amyotrophic lateral sclerosis (ALS).

The GTPase-Activating Protein SH3 Domain-Binding Proteins (G3BPs), G3BP1, G3BP2a and G3BP2b, are important regulators of stress granule dynamics. G3BP1 has been reported to play a critical role in the secondary aggregation step of stress granule formation, and has been used as a reliable marker of stress granules. The misregulation of stress granule dynamics has been reported in many forms of ALS. G3BP1 is critical for neuronal survival since G3BP1 null mice demonstrate widespread neuronal cell death in the central nervous system. Although single knockdown of either G3BP1 or G3BP2 partially reduces the number of stress granule-positive cells induced under stress conditions, the knockdowns of both genes significantly reduces the number. As such, G3BP1 and G3BP2 function redundantly in stress granule assembly.

G3BP1 and G3BP2 have been shown to interact with ubiquitin specific protease 10 (USP10) and Caprin1 (Kedersha, et al. (2016) *J. Cell Biol.* 212(7):845-60; Reineke, et al. (2015) *mBio* 6(2):e02486; Solomon, et al. (2007) *Mol. Cell Biol.* 27(6):2324-42; Soncini, et al. (2001) *Oncogene* 20(29):3869-79). USP10's interaction with G3BP1 involves an FGDF (SEQ ID NO:1) sequence within USP10 that binds a pocket within the N-terminal Nuclear Transport Factor 2-like (NTF2L) domain of G3BP1, and this binding inhibits stress granule condensation in response to some stresses (Kedersha, et al. (2016) *J. Cell Biol.* 212(7):845-60; Panas, et al. (2015) *PLoS Pathog.* 11(2):e1004659). Caprin1 competes with USP10 for binding to G3BP1, thus favoring stress granule condensation (Kedersha, et al. (2016) *J. Cell Biol.* 212(7):845-60).

SUMMARY OF THE INVENTION

This invention provides a method for identifying a lead or candidate compound that modulates the activity of GTPase-Activating Protein SH3 Domain-Binding Proteins (G3BP) by contacting a test compound with a N-terminal Nuclear Transport Factor 2-like (NTF2L) domain of G3BP (e.g., having the amino acid sequence of SEQ ID NO:2 or SEQ ID NO:3) and a peptide containing a FGDF motif (e.g., having the amino acid sequence of SEQ ID NO:4 or SEQ ID NO:5) for a period of time; and measuring whether the compound modulates the interaction between the NTF2L domain and the peptide containing a FGDF motif thereby identifying a lead or candidate compound that modulates the activity of G3BP. In one embodiment, the peptide containing a FGDF motif is conjugated to a fluorescent acceptor moiety. In certain embodiments, the step of measuring whether the compound modulates the interaction between the NTF2L domain and the peptide containing a FGDF motif includes Time Resolved Fluorescence Resonance Energy Transfer (TR-FRET).

DETAILED DESCRIPTION OF THE INVENTION

G3BP proteins function as scaffolds for stress granule formation and the NTF2L domain of G3BP1 (amino acid residues 1-142) integrates multiple regulatory signals through protein-protein interactions. A screening assay, in particular a fluorescence-based screening assay such as fluorescence polarization (FP) and time-resolved fluorescence resonance energy transfer (TR-FRET), has now been developed, which uses the NTF2L-FGDF peptide interaction as a target to identify compounds that bind G3BP and modulate G3BP function thereby modulating stress granule assembly. While activators may be of use in studying stress granule assembly, inhibitory compounds are expected to be therapeutically beneficial for a variety of diseases, including neurodegenerative diseases, viral infection, autoimmune disorders and tumorigenesis. Moreover, in so far as G3BP1 is involved in coordinating other important, disease-relevant activities that are independent of stress granule assembly, such as viral replication, cGAS activation, regulation of cancer metastasis and more, direct inhibitors of G3BP1 may be of use in inhibiting one or more these activities as well.

The invention is based on monitoring and/or measuring a molecular interaction (e.g., complex formation or disruption) between two binding partners, i.e., the NTF2L domain and a peptide containing the FGDF motif. In particular, the present invention provides a method of identifying lead or candidate compounds useful for modulating G3BP protein-protein interactions and for treatment of diseases or conditions associated G3BP protein-protein interactions, wherein the method includes screening test compounds against the NTF2L-FGDF motif binding partners using a competitive assay such as fluorescence polarization (FP) or TR-FRET. As used herein, "binding partner" is a compound (e.g., a first binding partner) that has affinity for another compound (e.g., a second binding partner) (or vice versa) such that the two binding partners are capable of forming a complex when bound.

The method of identifying a lead or candidate compound includes the steps of contacting a test compound or library of test compounds with a NTF2L domain and a peptide containing a FGDF motif for a period of time; and measuring whether the compound(s) modulates the interaction between the NTF2L domain and peptide containing a FGDF motif. Compounds that increase or enhance the interaction between the NTF2L domain and peptide containing a FGDF motif are of use in activating G3BP whereas compounds that decrease or diminish the interaction between the NTF2L domain and peptide containing a FGDF motif are of use in inhibiting G3BP function and stress granule assembly.

For the purposes of this invention, "GTPase-Activating Protein SH3 Domain-Binding Protein" or "G3BP" is intended to include the proteins G3BP1, G3BP2a, and G3BP2b. G3BP2a and G3BP2b are encoded by the same gene and represent alternatively spliced isoforms that differ by an insertion of 99 base pairs in the central region of G3BP2a giving rise to the presence of five SH3-binding domains in G3BP2b compared to four domains in the G3BP2a protein. The amino acid sequence of wild-type human G3BP1 is known in the art and available under GENBANK Accession Nos. NP_005745 and NP_938405. Likewise, the amino acid sequences of wild-type human G3BP2a and human G3BP2b are known in the art and available under GENBANK Accession Nos. NP_036429 and NP_987100, respectively.

G3BP1, G3BP2a, and G3BP2b are highly conserved across species. For example, there is 65% identity and 74% sequence similarity between G3BP1 and G3BP2a proteins in mice and humans. In this respect, this invention also includes the use of both human and non-human G3BP proteins. In particular, this invention includes G3BP proteins from various animals including chimpanzee, mouse, rat, and the like. Preferably, the animal is a mammal. Examples of wild-type mammalian G3BP proteins are known in the art and available under the GENBNAK Accession Nos. provided in Table 1.

TABLE 1

| | GENBANK Accession No. | |
|---|---|---|
| Animal | G3BP1 | G3BP2 |
| Pan troglodytes | JAA44555 | JAA39401 |
| | | JAA39402 |
| Macaca mulatta | NP_001248671 | AFE81132 |
| | | NP_001248697 |
| Canis lupus | XP_867372 | XP_022269103 |
| | | XP_022269104 |
| Mus musculus | NP_038744 | NP_001074266 |
| | | NP_001074265 |
| Bos taurus | NP_001032700 | NP_001039920 |
| | | XP_015327172 |
| Rattus norvegicus | NP_598249 | EDL88604 |
| | | NP_001014011 |

Wild-type G3BP proteins feature a highly conserved N-terminal Nuclear Transport Factor 2-like (NTF2L) domain. The NTF2L domain has been implicated in several G3BP functions including dimerization and stress granule assembly (Tourriere, et al. (2003) *J. Cell Biol.* 160:823-831). In addition, the G3BP NTF2L domain has been suggested to play a role in nuclear shuttling. This suggestion is based on findings of G3BP1 and G3BP2 both in the cytoplasm and in the nucleus (Barnes, et al. (2002) *Cancer Res.* 62:1251-1255; French, et al. (2002) *Histochem. J.* 34:223-231). As is known in the art, the NTF2L domain of G3BP is located within the N-terminal-140 amino acid residues of G3BP. An NTF2L domain of use in this invention is provided in Table 2.

TABLE 2

| G3BP | NTF2L domain sequence | SEQ ID NO: |
|---|---|---|
| 1 | MVMEKPSPLLVGREFVRQYYTLLNQAPDMLHRFYG KNSSYVHGGLDSNGKPADAVYGQKEIHRKVMSQNF TNCHTKIRHVDAHATLNDGVVVQVMGLLSNNNQAL RRFMQTFVLAPEGSVANKFYVHNDIFRYQDEVFGG FV | 2 |
| 2 | MVMEKPSPLLVGREFVRQYYTLLNKAPEYLHRFYG RNSSYVHGGVDASGKPQEAVYGQNDIHHKVLSLNF SECHTKIRHVDAHATLSDGVVVQVMGLLSNSGQPE RKFMQTFVLAPEGSVPNKFYVHNDMFRYEDEVFGD SE | 3 |

Ubiquitin specific protease 10 (USP10) acts as an oncogene or a tumor suppressor by regulating various protein substrates, including FLT3, p53, AMPK, PTEN, etc. Under energy stress conditions, USP10 specifically removes ubiquitination on AMPKα and promotes AMPKα phosphorylation. Meanwhile, AMPKα phosphorylation stimulates USP10 activation by phosphorylating Ser76 of USP10, thus forming a feedforward loop between USP10 and AMPK, ensuring amplification of AMPK activation. In addition, USP10 binds G3BP proteins via the peptide Phe-Gly-Asp-Phe (SEQ ID NO:1) (referred to herein as the "FGDF motif") and inhibits stress granule formation. It has been suggested that USP10 binding to G3BP stabilizes a soluble conformation of G3BP bound to 40S subunits (via G3BP C terminus) and to PABP (through USP10), causing SG disassembly (Kedersha, et al. (2016) *J. Cell Biol.* 212(7):845-60).

Non-structural protein 3 (NsP3) of alphaviruses is an essential component of viral RNA replicase and is important for negative sense and subgenomic RNA synthesis. Early in infection, alphavirus infection causes the formation of stress granules via the detection of dsRNA replication intermediates by protein kinase R leading to the phosphorylation of eIF2α. As the infection cycle progresses stress granules are disassembled. For Old World alphaviruses, the mechanism of stress granule disassembly involves the sequestration of G3BP by NsP3. NsP3 binds to the NTF2L domain of G3BP via its two FGDF motifs (SEQ ID NO:1). Upon binding by NsP3, G3BP is sequestered to viral replication complexes and other sites of viral protein aggregation. It has been proposed that the NsP3-G3BP oligomers function to stabilize viral replication complexes, by tying them together and thereby inducing high local concentrations of viral factors and in addition forming a protective layer against cellular antiviral mechanisms (Schulte, et al. (2016) *Open Biol.* 6:160078).

A peptide containing a FGDF motif in accordance with this invention may be derived from USP10 or NsP3. These peptides have been shown to interact with the NTF2L domain of G3BP. Thus, peptides of particular use in this invention include, but are not limited to a peptide having the amino acid sequence GALHSPQYIFGDFSPDEFNQFFVT (SEQ ID NO:4) or LTFGDFDEHEVDALASGITFGDFDD (SEQ ID NO:5). However, it is contemplated that a peptide containing a FGDF motif can be as few as 6 amino acid residues and as many as 40 amino acid residues. In this respect, the peptide containing a FGDF motif of this invention can be 6 to 40 amino acid residues, 8 to 38 amino acid residues, 10 to 36 amino acid residues, 12 to 34 amino acid residues, 14 to 32 amino acid residues, 16 to 30 amino acid residues, 18 to 28 amino acid residues, or 20 to 26 amino acid residues in length. In certain embodiments, the peptide containing a FGDF motif of this invention comprises, consists, or consists essentially of the amino acid sequence GALHSPQYIFGDFSPDEFNQFFVT (SEQ ID NO:4) or LTFGDFDEHEVDALASGITFGDFDD (SEQ ID NO:5).

The NTF2L domain and peptide containing a FGDF motif can be prepared by conventional recombinant DNA methods. In general, this includes isolating the nucleic acid molecule encoding the protein of interest (e.g., by restriction enzyme digestion or PCR amplification); inserting the coding sequence of protein of interest (in frame) into a suitable vector, e.g., an expression vector that includes the requisite sequences for protein expression (e.g., promoter, terminator, etc.); and introducing the vector into a suitable host cell, e.g., to express the fusion protein.

The terms "nucleic acid molecule" and "polynucleotide" are used interchangeably and refer to a polymeric form of nucleotides of any length, either deoxyribonucleotides or ribonucleotides, or analogs thereof. Non-limiting examples of nucleic acid molecules include a gene, a gene fragment, exons, introns, messenger RNA (mRNA), transfer RNA, ribosomal RNA, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

In particular, the nucleic acid molecules of the invention encode the NTF2L domain and peptides containing a FGDF motif disclosed herein. A "coding sequence" or a sequence that "encodes" a selected polypeptide, is a nucleic acid molecule which can be transcribed (in the case of DNA) and translated (in the case of mRNA) into a polypeptide, for example, in a host cell when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from mRNA, genomic DNA sequences, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

To facilitate amplification and expression, the nucleic acid molecule encoding the protein of interest may be inserted into a vector. A "vector" is capable of transferring gene sequences to a host cell. Typically, "vector," "expression vector," and "gene transfer vector," mean any nucleic acid construct capable of directing the expression of a gene of interest and which can transfer gene sequences to host cells, which can be accomplished by genomic integration of all or a portion of the vector, or transient or inheritable maintenance of the vector as an extrachromosomal element. Thus, the term includes cloning, and expression vehicles, as well as integrating vectors.

A number of expression vectors for the expression of a nucleic acid molecule encoding a protein are known in the art. Different examples of expression vectors are available for expression of the protein in mammalian cells, insect cells, yeast cells, and bacterial cells. Non-limiting examples of publicly-available mammalian expression vectors include constitutive expression vectors GATEWAY® pDEST™26, pDEST™27, pDEST™40, and pDEST™47 (Invitrogen); adenoviral expression vectors (e.g., pAd/CM/V5-Dest GATEWAY® Vector Kit (Invitrogen); episomal expression vectors pCEP4 and pEBNA DEST (Invitrogen); lentiviral expression vectors (e.g., VIRAPOWER™ Bsd; Invitrogen); and regulated expression vectors GATEWAY® pT-REX™-DEST 30 and pT-REX™-DEST 31 (Invitrogen). Non-limiting examples of bacterial expression vectors include GATEWAY® vectors pDEST™14, pDEST™15, pDEST™17, pDEST™24, pET-DEST42; pEM7/Bsd; pEM7/Zeo; pRSET A, B, & C; pRSET-BFP; pRSET-CFP; pRSET-EmGFP; pTrcHIs A, B, & C; and pTrcHIs2 A, B, & C vectors (Invitrogen). Non-limiting examples of yeast expression vectors include pAO815; pGAPZ A, B, & C; pPIC3.5K; pPIC9K; pTEFl/Bsd; pTEFl/Zeo; pYC2/CT; pYES2; pYES2/CT; and pYES3/CT (Invitrogen). Non-limiting examples of insect and baculovirus expression vectors include GATEWAY® vectors pDEST™10, pDEST™20, pDEST™8, pMT-DEST™48; pAC5.1/V5-His A, B, & C; pFastBac Dual; and pIB/V5-His-DEST (Invitrogen).

The expression vectors used to express a protein may include one or more (e.g., 1, 2 or 3) constitutive promoter sequences and/or one or more (e.g., 1, 2 or 3) inducible promoter sequences. Non-limiting examples of constitutive promoter sequences include bacterial promoters (e.g., E. coli $a^{70}$, $\sigma^s$, $\sigma^{32}$, or $\sigma^{54}$ promoters; B. subtilis $\sigma^A$ or $\sigma^B$ promoters; T7 RNA polymerase-based promoters; and a bacteriophage SP6 promoter), yeast promoters (e.g., pCyc, pAdh, pSte5, ADH1, cyc70, cyc43, cyc28, pPGK1, pCYC, and GPD (TDH3) promoters), and mammalian promoters (e.g., cytomegalovirus immediate early gene-based promoters, SV40 early promoter, and Rous sarcoma virus promoter). Non-limiting examples of inducible promoter sequences include alcohol dehydrogenase I gene promoters, tetracycline-responsive promoter systems, glucocorticoid receptor promoters, estrogen receptor promoter, ecdysone receptor promoters, metallothionein-based promoters, and T7-polymerase based promoters. Several different mammalian expression vectors available that allow for the inducible expression of a nucleic acid sequence are publicly available including pTET-ON Advanced (Clontech), pERV3 (Stratagene), pNEBR-R1 (New England BioLabs), and pCMV5-CymR (Qbiogene).

One or more nucleic acid molecules encoding a protein of the invention may be introduced into a transgenic cell or host cell using methods known in the art, including, but not limited to electroporation, microinjection, lipid-mediated transfection (e.g., liposomal delivery systems), calcium phosphate-mediated transfection, DEAE dextran-mediated transfection, DNA transfection by biolistics, DNA transfection mediated by polybrene, and virus-mediated transduction.

Any type of cell or host cell can be used in accordance with this invention, including, but not limited to, a mammalian cell (e.g., a human, mouse, rat, monkey, or rabbit cell), a yeast cell, a bacterial cell, or an insect cell. A mammalian cell that expresses a protein of the invention may include a primary cell such as a fibroblast, an epithelial cell, an endothelial cell, a smooth muscle cell, a hepatocyte, a kidney cell, and a lymphocyte. Additional examples of suitable mammalian cell lines include COS-7 monkey kidney cells, CV-1, L-cells, C127 cells, 3T3 cells, Chinese hamster ovary (CHO) cells, human embryonic kidney (HEK) cells, HeLa cells (e.g., HeLa S3 or HeLa Kyoto cells), 293 cells, 293T cells, N2A, U20S, HUH7 and BHK cell lines. A variety of cells are commercially available for the expression of recombinant proteins, including, but not limited to, bacterial competent cells (e.g., BL21-AI™ ONE SHOT®, ONE SHOT®-BL21(DE3), and ONE SHOT®-BL21(DE3) pLysE, (Invitrogen); and mammalian competent cells (e.g., MAXPAK Competent HeLa S3 cells, MAXPAK Competent CHO-K1 cells, and MAXPAK Competent HEK 293 cells (Genlantis)).

A transgenic cell that contains a nucleic acid molecule encoding a protein of this invention may a stable cell line (e.g., a cell that has integrated the nucleic acid molecule encoding the protein into one or more of its chromosomes). Alternatively, a transgenic cell may contain the nucleic acid molecule encoding the protein in a plasmid or on an artificial chromosome, which replicates independently of the chromosomes of the cell.

A transgenic mammal may also be produced from a transgenic cell containing a nucleic acid molecule encoding a protein of this invention. A transgenic animal may be a mouse, a rat, a bovine, an ovine, a caprine, a porcine, a horse, a rabbit, or a monkey. Methods for the production of a transgenic mammal from a transgenic cell are known in the art and include, without limitation, methods that require the transfer of a nucleus from a transgenic cell to an enucleated oocyte and/or the microinjection of one or more nucleic acids (e.g., a plasmid or an artificial chromosome) encoding the proteins into an oocyte. Such genetically manipulated oocytes may then be transferred into a recipient female host to produce a transgenic mammal.

Alternatively, the NTF2L domain and/or peptide containing a FGDF motif can be synthesized chemically using standard solid phase synthesis techniques. See, e.g., Merrifield (1963) *J. Amer. Chem. Soc.* 85:2149-2154; or Fields, et al. (1992) *Principles and practice of solid-phase peptide synthesis*, pages 77-183 in *Synthetic Peptides: A Users Guide*, Freeman and Co., New York. For ease of synthesis and cost considerations, it is preferred that polypeptides synthesized chemically have between 3 to 50 amino acids (e.g., 3 to 30 amino acids in length). Once synthesized or recombinantly expressed, the NTF2L domain and/or peptide containing a FGDF motif can be separated from chemical precursors or other reagents involved in the synthesis/expression of the protein and subsequently used in the method and kit of this invention. Suitable methods for purifying the polypeptides can include, for example, affinity chromatography, immunoprecipitation, size exclusion chromatography, and ion exchange chromatography. See, e.g., Flohe, et al. (1970) *Biochim. Biophys. Acta* 220:469-476; or Tilgmann, et al. (1990) *FEBS* 264:95-99. The extent of purification can be measured by any appropriate method, including but not limited to, column chromatography, polyacrylamide gel electrophoresis, or high-performance liquid chromatography.

In accordance with the method of this invention, the NTF2L domain and peptide containing a FGDF motif are contacted with a test compound or library of test compounds for a period of time (e.g., 10 minutes, 20 minutes, 30 minutes, 40 minutes, 50 minutes, 1 hour, 2 hours, 3 hours, or 4 hours) to allow for a test compound to enhance or disrupt the interaction between the NTF2L domain and peptide containing a FGDF motif. The test compound may be of a peptide, polypeptide, antibody, nucleic acid, lipid, carbohydrate, small organic molecule, or be obtained from a natural product extract library, e.g., isolated from an animal, plant, fungus and/or microbe. A library can have as few as two members or as many as $10^{12}$ members. In this respect, the assay can be carried out in a test tubes or with multiwell plates (e.g., 6-well plate, 24-well plate, 96-well plate, 384-well plate, 1536-well plate, 6144-well-plate, or 9600-well plate) and can include the use of a robotic and/or computer system to perform one or more of the following functions: (i) moving assay modules; (ii) shaking the assay modules (and assay contents therein); (iii) storing plates (e.g., refrigeration unit); (iv) liquid or reagent handling (e.g., mixing reagents); and (v) reagent delivery (e.g., dispensing reagents into wells, etc.).

Competitive assays for measuring whether a compound modulates the interaction between the NTF2L domain and peptide containing a FGDF motif includes one or more of the following.

Fluorescence Intensity (FI) Assay. Fluorescent probes are used in biochemistry to study the various binding sites in large macromolecules through the difference of the quenching rates of the bound verses free probe. Fluorescence intensity has been widely applied over the last two decades due to the vast development of new fluorophores. Typically, an optical system illuminates and excites the sample at a specific wavelength selected by a high performance optical filter. As a result, the sample emits light and a second optical system collects the emitted light. Usually, the emitted light is of lower energy and thus is composed of a longer wavelength than the excitation light.

(ii) Fluorescence Polarization (FP). Fluorescence polarization (or fluorescence anisotropy) measurements provide information on molecular orientation and mobility and processes that modulate them, including receptor-ligand interactions, protein-DNA interactions, and proteolysis. Because polarization is a general property of fluorescent molecules (with certain exceptions such as lanthanide chelates), polarization-based readouts are somewhat less dye dependent and less susceptible to environmental interferences such as pH changes than assays based on fluorescence intensity measurements. Experimentally, the degree of polarization is determined from measurements of fluorescence intensities parallel and perpendicular with respect to the plane of linearly polarized excitation light, and is expressed in terms of fluorescence polarization (P) or anisotropy (r).

(iii) Time Resolved Fluorescence (TRF). TRF detection differs from fluorescence intensity (FI) in the timing of the excitation/emission (measurement) process. In case of standard FI the excitation and emission processes are within a time frame of nanoseconds: namely, the light emitted by the sample is measured right after the excitation. Every fluorophore has a fluorescence lifetime and the decay curve of the excitation wavelength energy will contribute differently to the background activity of the emission wavelength being measured. The use of long-lifetime fluorophores such as rare earth elements called lanthanides, particularly uropium, Gadolinium, Terbium and Samarium, minimizes the problem of background fluorescence since lanthanides have an unusual property of emitting light over long periods of time after excitation—up to milliseconds rather than nanoseconds as in standard FI. Complexes of the rare earth ions with macromolecules are preferably used in TRF since they have large Stoke's shifts and extremely long emission half-lives when compared to more traditional fluorophores.

(iv) Fluorescence Resonance Energy Transfer (FRET). FRET is a distance-dependent interaction between the electronic excited states of two dye molecules in which excitation is transferred from a donor molecule to an acceptor molecule without emission of a photon. The efficiency of FRET is dependent on the inverse sixth power of the intermolecular separation, making it useful over distances comparable to the dimensions of biological macromolecules. Thus, FRET is an important technique for investigating a variety of biological phenomena that produce changes in molecular proximity. FRET is particularly advantageous as it is performed in a homogeneous format that is particularly amenable to high-throughput screening (HTS), since acceptor emissions, as a measure of energy transfer, can be detected without the need to separate bound from unbound assay components. When FRET is used as a contrast mechanism, colocalization of proteins and other molecules can be imaged with spatial resolution beyond the limits of conventional optical microscopy. The distance at which energy transfer is 50% efficient (i.e., 50% of excited donors are deactivated by FRET) is defined as the Förster radius ($R_0$). The magnitude of $R_0$ is dependent on the spectral properties of the donor and acceptor dyes and their spatial arrangement.

(v) Time Resolved-FRET (TR-FRET). TR-FRET, known also as homogeneous time-resolved fluorescence (HTRF®), unites TRF (time-resolved fluorescence) and FRET (fluorescence resonance energy transfer) principles. This combination brings together the low background benefits of TRF with the homogeneous assay format of FRET. This powerful combination provides significant benefits to drug discovery researches including assay flexibility, reliability, increased assay sensitivity, higher throughput and fewer false positive/false negative results. For screening libraries of compounds, TR-FRET is a recognized method for overcoming interference from compound autofluorescence or light scatter from precipitated compounds.

The premise of a TR-FRET assay is the same as that of a standard FRET assay, i.e., when a suitable pair of fluorophores are brought within close proximity of one another, excitation of the first fluorophore (the donor) can result in energy transfer to the second fluorophore (the acceptor). This energy transfer is detected by an increase in the fluorescence emission of the acceptor, and a decrease in the fluorescence emission of the donor. In HTS assays, FRET is often expressed as a ratio of the intensities of the acceptor and donor fluorophores. The ratiometric nature of such a value corrects for differences in assay volumes between wells, and corrects for quenching effects due to colored compounds.

In contrast to standard FRET assays, TR-FRET assays use a long-lifetime lanthanide ions chelate or cryptates as the donor species, thereby achieving particularly extended duration, in the order of milliseconds or longer of the average time that the donor molecule spends in the excited state after accepting a photon. This is in sharp contrast to the lifetime of common fluorophores used in standard FRET assays, which are typically in the nanosecond range. Because interference from autofluorescent compounds or scattered light is also on the nanosecond timescale, these factors can negatively impact standard FRET assays. To overcome these interferences, TR-FRET assays are performed by measuring FRET after a suitable delay, typically 50 to 100 microseconds after excitation. This delay not only overcomes interference from background fluorescence or light scatter, but also avoids interference from direct excitation due to the non-instantaneous nature of the flash lamp excitation source.

(vi) DELFIA. Dissociation-enhanced lanthanide fluorescent immunoassay (DELFIA) is a robust, high-performance immunodetection platform that provides a combination of benefits that make it the superior alternative to conventional ELISA. DELFIA uses the unique chemical properties of the long-lived lanthanide chelates as the tracer, mostly europium chelate fluorophores, in concert with time-resolved fluorescence (TRF) detection to create an assay that may significantly increase the signal window when compared to ELISA.

(vii) SPA. Scintillation Proximity Assay (SPA), is performed using low energy radioisotopes ($^3$H and $^{125}$I) as labels due to their short-range electron emission, and microscopic beads containing a scintillant which emits light when it is stimulated. Stimulation occurs when radio-labeled molecules interact and bind to the surface of the bead. This interaction will trigger the bead to emit light photons, which can be detected using a scintillation counting. Electrons emitted from labeled molecules not close to the surface of the beads dissipate their energy and are not detected. This binding assay has the advantage of avoiding the usual filtration or washing procedures.

In certain aspects of this invention, the step of measuring whether a compound modulates the interaction between the NTF2L domain and peptide containing a FGDF motif includes the use of TR-FRET. In accordance with this aspect, the peptide containing a FGDF motif is labeled with a fluorescent acceptor moiety and a metal liganding moiety is conjugated to an antibody that binds to the NTF2L domain, in particular a tag fused to the NTF2L domain. Tags that may be fused (in-frame) with the N- or C-terminus of the NTF2L domain include but are not limited to, V5, myc, $His_6$ (SEQ ID NO:6), FLAG®, glutathione-S-transferase (GST), the Fc portion of human IgG, and maltose binding protein (MEP). Preferably, the tag is a GST tag fused to the N-terminus of the NTF2L domain.

A metal liganding moiety coordinates one or more lanthanide metal ions to form a metal complex containing Tb(III). Typically, a metal liganding moiety includes one or more metal coordinating moieties X, where X is a heteroatom electron-donating group capable of coordinating a metal cation, such as $O^-$, $OH$, $NH_2$, $OPO_3^{2-}$, NHR, or OR where R is an aliphatic group. A metal liganding moiety can be a chelating moiety or a cryptand moiety. If a lanthanide metal ion is coordinated to a chelating moiety, the complex is referred to as a "metal chelate." If a lanthanide metal ion is coordinated to a cryptand moiety, the complex is referred to as a "metal cryptand." A metal chelate should be stable to exchange of the lanthanide ion. Metal chelates preferably have a formation constant ($1 <_f$) of greater than $10^{10}$ $M^{-1}$. A variety of useful chelating moieties are known to those of skill in the art. Typical examples of chelating moieties include: EDTA, DTPA, TTHA, DOTA, NTA, HDTA, DTPP, EDTP, HDTP, NTP, DOTP, DO3A, DOTAGA, and NOTA. Chelating and cryptand moieties can be synthesized by a variety of methods known to those of skill in the art or may be purchased commercially. See U.S. Pat. Nos. 5,656,433; 5,622,821; 5,571,897; 5,534,622; 5,220,012; 5,162,508; and 4,927,923.

Metal liganding moieties coordinate one or more lanthanide metal ions to form a metal complex containing Tb(III) Lanthanide metal ions are useful because their special electronic configuration shields the optically active electrons, resulting in characteristic line type emissions. As the electronic transitions of the metal ions are forbidden by quantum mechanics rules, the emission lifetimes of these ions are typically long (from µs to msec). Useful lanthanide metal ions include Sm(III), Ru(III), Eu (III), Gd(III), Tb(III), and Dy(III). The metal complexes useful in the invention contain Tb(III). Methods for complexing a metal ion to a chelating or cryptand moiety are known to those of skill in the art, see, e.g., WO 96/23526 and WO 03/011115.

Tag-specific antibodies including metal liganding moieties may be prepared by conventional methods or purchased from a commercial source. For example, ThermoFisher Scientific provides a LanthaScreen™ Tb-anti-GST Antibody, LanthaScreen™ Eu-anti-GST Antibody, LanthaScreen™ Eu-anti-His Antibody, and LanthaScreen™ Eu-anti-FLAG® Antibody.

A fluorescent acceptor moiety can act as an acceptor in RET or TR-FRET-based assays and/or can be a fluorophore for which the polarization of fluorescence emission is measured in an FP-based assay. In general, a fluorescent acceptor moiety should exhibit a good quantum yield and a large extinction coefficient; should be resistant to collisional quenching and bleaching; and should be easily conjugated to a protein of interest (i.e., a peptide containing a FGDF motif) by methods known to those having ordinary skill in the art.

Exemplary fluorescent acceptor moieties include, but not limited to, fluorescein, rhodamine, GFP, GFP derivatives, FITC, 5-carboxyfluorescein (5-FAM), 6-FAM, 7-hydroxycoumarin-3-carboxamide, 6-chloro-7-hydroxycoumarin-3-carboxamide, fluorescein-5-isothiocyanate, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, and 7-amino-4-methylcoumarin-3-acetic acid. GFP and GFP mutants are particularly useful in applications using Tb(III)-containing metal complexes. A variety of mutants of GFP from *Aequorea victoria* have been created that have distinct spectral properties, improved brightness, and enhanced expression and folding. See, e.g., U.S. Pat. Nos. 5,625,048; 5,777,079; and 5,804,387. Methods for incorporating fluorophores into a variety of binding partners are known to those of skill in the art. See, e.g., U.S. Pat. No. 6,410,255.

Once a compound has been identified as modulating (increasing or decreasing) the interaction between the NTF2L domain and peptide containing a FGDF motif, the compound may be tested in one or more in vitro models or animal models for the ability to inhibit or reduce the activity of G3BP and prevent or treat a neurodegenerative disease, viral infection, autoimmune disorder or tumorigenesis.

A compound exhibiting the desired activity can be provided in a pharmaceutical composition suitable for use in human beings and animals. In this respect, the compound can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. The compound can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms.

The dosage regimen for the compounds of the present invention will vary depending upon known factors, such as the pharmacodynamic characteristics of the particular agent and its mode and route of administration; the species, age, sex, health, medical condition, and weight of the recipient; the nature and extent of the symptoms; etc.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day.

The invention is described in greater detail by the following non-limiting examples.

Example 1: Materials and Methods

Materials. Terbium-labeled anti-glutathione-S-transferase (Tb-anti-GST) antibody, Tris-HCl (pH 7.5) and dithiothreitol (DTT) were purchased from Life Technologies (Carlsbad, Calif.). $MgCl_2$ was purchased from Boston BioProducts (Ashland, Mass.). Bovine serum albumin (BSA) was purchased from Sigma-Aldrich (St. Louis, Mo.). Dimethyl sulfoxide (DMSO) and Multidrop™ Combi were purchased from Fisher Scientific (Atlanta, Ga.). Black 384-well low-volume plates and 384-well compound plates were purchased from Corning Life Sciences (Tewksbury, Ma.). Pin tools were purchased from V&P Scientific, Inc. (San Diego, Calif.).

GST-NTF2L. Residues 1-142 of G3BP1 (SEQ ID NO:2) were fused to GST and the resulting fusion protein was expressed and purified from *E. coli*. In particular, *E. coli* harboring nucleic acids encoding the GST-NTF2L fusion protein were grown to OD600 of 0.8 and induced with 0.6 mM IPTG at 16° C. overnight. Pelleted cells were resuspended in lysis buffer (250 mM NaCl, 50 mM HEPES 7.5, 1 mM DTT, protease inhibitor). After sonication, lysates were pelleted at 30,000×g at 4° C. for 30 minutes. Supernatants were applied to packed GST columns with 10 ml GST beads (GE) prewashed with lysis buffer at room temperature. Proteins were eluted with 10 mM glutathione (Sigma) in lysis buffer. The proteins were further purified by gel filtration material sold under the trademark SUPERDEX® 200 16/200 (GE) equilibrated in SEC buffer (400 mM NaCl, 50 mM HEPES 7.5, 1 mM DTT). The fractions were analyzed by SDS-PAGE, pooled, concentrated, filtered and stored at −80° C.

USP10 Peptides. USP10-derived peptides were synthesized including FAM-USP10_24 peptide: 5-FAM-PEG6-GALHSPQYIFGDFSPDEFNQFFVT (SEQ ID NO:7) and unlabeled control USP10_24 peptide: GALHSPQYIFGDFSPDEFNQFFVT (SEQ ID NO:4).

Chemical Library. The St. Jude bioactive and FDA drug collection containing 11,297 chemicals with 5000 unique chemical identities (PMID: 29146910) were plated in 384-well compound plates from columns 3 to 12 and columns 15 to 24.

TR-FRET Assay. The TR-FRET assay was performed in black 384-well low-volume plates with 20 μl assay volume/well at room temperature. The assay buffer was composed of 50 mM Tris-HCl (pH 7.5), 20 mM $MgCl_2$, 0.1 mg/mL BSA, and 1 mM DTT. All peptides and chemicals were solubilized with DMSO. The final DMSO concentration was 1.1% in the experiments to measure $K_d$ values of FAM-USP10_24 peptide binding to GST-NTF2L, and the inhibitory activity of unlabeled USP10_24 peptide to disrupt the interaction between FAM-USP10_24 and GST-NTF2L. The final DMSO concentration was 0.15% in the chemical library screening. After all assay components were mixed, plates were always shaken with an IKA MTS 2/4 digital microtiter shaker (Wilmington, N.C.) at 700 rpm for 1 minute and spun down in an Eppendorf 5810 centrifuge with the A-4-62 swing-bucket rotor (Eppendorf AG, Hamburg, Germany) for 30 seconds. All TR-FRET assay signals were measured with a PHERAstar® FS plate reader (BMG Labtech, Durham, N.C.) for the fluorescence emission ratio (10,000×520 nm/490 nm) of each well, using a 340-nm excitation filter, a 100-μs delay, and a 200-μs integration time. In the FAM-USP10_24 peptide $K_d$ determination and USP10_24 peptide inhibitory activity test, the raw counts from the PHER-Astar® FS plate reader were input to the GraphPad Prism 8.0.1 data analysis software (GraphPad Software, La Jolla, Calif.) to plot curves and derive $K_d$ and $IC_{50}$ values. In the chemical library screening, the signal from the positive control peptide USP10_24 at 15 μM with 0.15% DMSO was defined as 100% inhibition and the signal from the 0.15% DMSO was defined as 0% inhibition, respectively. The activities of tested chemicals were normalized to that of positive and negative controls by following equation 1.

$$\text{Inhibition of Chemical \%} = 100\% \times \left( \frac{Signal_{Negative} - Signal_{Chemical}}{Signal_{Negative} - Signal_{Positive}} \right) \quad \text{Equation 1}$$

$K_d$ Measurement of FAM-USP10_24 peptide to GST-NTF2L. FAM-USP10_24 peptide (1-to-2 dilutions with concentrations ranged from 20 μM to 1.22 nM) was incubated with 2 nM Tb-anti-GST, with or without 2 nM GST-NTF2L. The TR-FRET signals of individual wells were collected at incubation time points of 30 minutes, 60 minutes, 90 minutes, 120 minutes, 150 minutes, 180 minutes, 240 minutes and 300 minutes and the values were fitted by the GraphPad Prism software with the one-site total binding equation for the FAM-USP10_24 peptide along with Tb-anti-GST and GST-NTF2L group or the FAM-USP10_24 peptide along with Tb-anti-GST, but without GST-NTF2L group. The individual dissociation constant ($K_d$), if applicable, was then derived from the FAM-USP10_24 peptide along with Tb-anti-GST and GST-NTF2L group.

Determination the Inhibitory Activity of the USP10_24 Control Peptide Against the TR-FRET Binding Assay Between FAM-USP10_24 Peptide and GST-NTF2L. USP10_24 peptide (1-to-2 dilutions with concentrations ranged from 20 μM to 0.61 nM) was incubated with 84 nM FAM-USP10_24, 2 nM Tb-anti-GST, 2 nM GST-NTF2 for 120 minutes. The TR-FRET signals from individual wells were collected and the values were fitted by the GraphPad Prism software with the sigmoidal dose-response equation to derive $IC_{50}$ values.

Primary Screening Against Test Compounds. In the TR-FRET primary screen to identify compounds that disrupt the interaction between FAM-USP10_24 and GST-NTF2L, GST-NTF2L (2.66 nM, 15 μl/well) or buffer (without GST-NTF2L group) was first dispensed with Multidrop™ Combi to black 384-well low-volume plates. After a brief spin down, chemicals (10 mM DMSO stock), USP10_24 control peptide (10 mM or 1-to-2 dilutions with concentrations ranged from 20 mM to 610 nM), or DMSO were transferred to individual wells using a pin tool at 30 nl/well. The plates were incubated for 30 minutes after spinning down and brief shaking. A mixture of Tb-anti-GST (8 nM) and FAM-USP10_24 (336 nM) was then dispensed with Multidrop™ Combi (5 μl/well). The final chemical concentration tested was 15 μM. The final USP10_24 peptide concentration was 15 μM (positive control group) or 30 μM to 0.92 nM (reference group). The DMSO group was served as the negative control group (0% inhibition). The without GST-NTF2L group served as an extra control group, but not used in data normalization to derive % Inhibition for tested chemicals. The plates were then incubated for 120 minutes after spinning down and brief shaking. The TR-FRET signals from individual wells were collected and the values were converted to % Inhibition by following the Equation 1 with the USP10_24 peptide group (15 μM) and the DMSO group served as respective positive (100% inhibition) and negative (0% inhibition) controls.

Example 2: Affinity of FAM-USP10_24 for GST-NTF2L

The FAM-USP10_24 peptide was tested for its binding affinity to GST-NTF2L by a TR-FRET binding assay in the presence of Tb-anti-GST. In the TR-FRET binding assay, the FAM-USP10_24 has high TR-FRET interaction signal and high affinity to the GST-NTF2L with the $K_d$ values of 145.2 nM (30-minute incubation time), 118.1 nM (60-minute incubation time), 105.2 nM (90-minute incubation time), 84.1 nM (120-minute incubation time), 85.9 nM (150-minute incubation time), 82.3 nM (180-minute incubation time), 82.0 nM (240-minute incubation time), 85.0 nM (300-minute incubation time). The $K_d$ values were very consistent from the 120-minute to 300-minute incubation times. The 120-minute incubation time were selected for further experiments. On the other hand, the without GST-NTF2L group that included FAM-USP10_24 and Tb-anti-GST, only had very low background TR-FRET interaction. The curves were basically a series of straight lines with signals generated from the non-specific interaction between the FAM-USP10_24 peptide and Tb-anti-GST. The signal intensities were low and proportionally to the concentrations of the FAM-USP10_24. The big TR-FRET signal difference between the top group of curves and the bottom groups of straight line clearly demonstrated the interaction was GST-NTF2L-mediated.

Example 3: Interaction Between FAM-USP10_24 Peptide and GST-NTF2L1 is Mediated by the USP10_24 Peptide To test if the interaction between FAM-USP10_24 and GST-NTF2L1 was indeed mediated by the USP10_24 peptide, the unlabeled USP10_24 peptide was tested against the interaction between FAM-USP10_24 and GST-NTF2L1 with concentrations ranged from 20 μM to 0.61 nM in 1-to-2 dilutions. In the test, unlabeled USP10_24 peptide inhibited the interaction between FAM-USP10_24 and GST-NTF2L1 in a dose-dependent manner with an $IC_{50}$ value of 475.9 nM (120-minute incubation time). This dose-dependent inhibition of USP10_24 peptide against the interaction between FAM-USP10_24 and GST-NTF2L1 demonstrated that the interaction is USP10_24 peptide-mediated and the unlabeled USP10_24 peptide effectively competes with the labeled peptide to disrupt the interaction with GST-NTF2L1.

Example 4: Identifying Inhibitors that Disrupt the Interaction Between USP10_24 and GST-NTF2L In an effort to identify small molecule inhibitors of the interaction between USP10_24 and GST-NTF2L, the St. Jude FDA drug and bioactive collection which included 11,297 chemicals with 5000 unique chemical identities was screened. The test had great performance with Z-Prime values of 0.87±0.04 and ranged from 0.78 to 0.95. A Z-Prime >0.5 indicates that the performance of the screen is acceptable (PMID: 10838414). The control peptide USP10_24 had a representative $IC_{50}$ value of 330 nM in the chemical screen. By using 30% inhibition as cutoff, 252 chemicals with 172 unique ones were selected as the primary hits for further confirmation in dose response analysis.

What is claimed is:

1. A method of identifying a lead or candidate compound that modulates the activity of GTPase-Activating Protein SH3 Domain-Binding Proteins (G3BP) comprising:
   (a) contacting a test compound in vitro with a N-terminal Nuclear Transport Factor 2-like (NTF2L) domain of G3BP and a peptide containing a FGDF motif for a period of time; and
   (b) measuring whether the compound modulates the interaction between the NTF2L domain and the peptide containing a FGDF motif thereby identifying a lead or candidate compound that modulates the activity of G3BP.

2. The method of claim 1, wherein the NTF2L domain has the amino acid sequence of SEQ ID NO:2 or SEQ ID NO:3.

3. A method of identifying a lead or candidate compound that modulates the activity of GTPase-Activating Protein SH3 Domain-Binding Proteins (G3BP) comprising:
   (a) contacting a test compound in vitro with a N-terminal Nuclear Transport Factor 2-like (NTF2L) domain of G3BP and a peptide containing a FGDF motif for a period of time; and
   (b) measuring whether the compound modulates the interaction between the NTF2L domain and the peptide containing a FGDF motif thereby identifying a lead or candidate compound that modulates the activity of G3BP,
   wherein the peptide containing a FGDF motif has the amino acid sequence of SEQ ID NO:4 or SEQ ID NO:5.

4. The method of claim 3, wherein the peptide containing a FGDF motif is conjugated to a fluorescent acceptor moiety.

5. The method of claim 3, wherein the step of measuring whether the compound modulates the interaction between the NTF2L domain and the peptide containing a FGDF motif comprises Time Resolved Fluorescence Resonance Energy Transfer (TR-FRET).

* * * * *

SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Phe Gly Asp Phe
1

<210> SEQ ID NO 2
<211> LENGTH: 142
<212> TYPE: PRT
<213> ORGANISM: Artificial Sequence
<220> FEATURE:
<223> OTHER INFORMATION: Synthetic peptide

<400> SEQUENCE: 2

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val
    130                 135                 140

<210> SEQ ID NO 3
<211> LENGTH: 142
<212> TYPE: PRT
<213> ORGANISM: Artificial Sequence
<220> FEATURE:
<223> OTHER INFORMATION: Synthetic peptide

<400> SEQUENCE: 3

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
            20                  25                  30

Phe Tyr Gly Arg Asn Ser Ser Tyr Val His Gly Val Asp Ala Ser
        35                  40                  45

Gly Lys Pro Gln Glu Ala Val Tyr Gly Gln Asn Asp Ile His His Lys
    50                  55                  60

Val Leu Ser Leu Asn Phe Ser Glu Cys His Thr Lys Ile Arg His Val
65                  70                  75                  80

Asp Ala His Ala Thr Leu Ser Asp Gly Val Val Gln Val Met Gly
                85                  90                  95

Leu Leu Ser Asn Ser Gly Gln Pro Glu Arg Lys Phe Met Gln Thr Phe
            100                 105                 110

Val Leu Ala Pro Glu Gly Ser Val Pro Asn Lys Phe Tyr Val His Asn
        115                 120                 125

Asp Met Phe Arg Tyr Glu Asp Glu Val Phe Gly Asp Ser Glu
    130                 135                 140

<210> SEQ ID NO 4
<211> LENGTH: 24
<212> TYPE: PRT
<213> ORGANISM: Artificial Sequence
<220> FEATURE:
<223> OTHER INFORMATION: Synthetic peptide

<400> SEQUENCE: 4

Gly Ala Leu His Ser Pro Gln Tyr Ile Phe Gly Asp Phe Ser Pro Asp
1               5                   10                  15

Glu Phe Asn Gln Phe Phe Val Thr
            20

<210> SEQ ID NO 5
<211> LENGTH: 25
<212> TYPE: PRT
<213> ORGANISM: Artificial Sequence
<220> FEATURE:
<223> OTHER INFORMATION: Synthetic peptide

<400> SEQUENCE: 5

Leu Thr Phe Gly Asp Phe Asp Glu His Glu Val Asp Ala Leu Ala Ser
1               5                   10                  15

Gly Ile Thr Phe Gly Asp Phe Asp Asp
            20                  25

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

His His His His His His
1               5

<210> SEQ ID NO 7
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 5-FAM-PEG6 labeled

<400> SEQUENCE: 7

Gly Ala Leu His Ser Pro Gln Tyr Ile Phe Gly Asp Phe Ser Pro Asp
1               5                   10                  15

Glu Phe Asn Gln Phe Phe Val Thr
            20